United States Patent
Frueh

(10) Patent No.: US 10,533,914 B2
(45) Date of Patent: Jan. 14, 2020

(54) PIPELINE SENSOR CARRIER

(71) Applicant: General Electric Company, Schenectady, NY (US)

(72) Inventor: Volker Frueh, Karlsruhe (DE)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/006,451

(22) Filed: Jun. 12, 2018

(65) Prior Publication Data
US 2018/0292285 A1    Oct. 11, 2018

Related U.S. Application Data

(63) Continuation of application No. 14/997,125, filed on Jan. 15, 2016, now Pat. No. 10,036,680.
(Continued)

(51) Int. Cl.
| | |
|---|---|
| G01N 29/265 | (2006.01) |
| F16L 55/40 | (2006.01) |
| G01M 3/00 | (2006.01) |
| G01N 29/04 | (2006.01) |
| G01N 29/22 | (2006.01) |

(Continued)

(52) U.S. Cl.
CPC .............. *G01M 3/005* (2013.01); *F16L 55/40* (2013.01); *F17D 5/06* (2013.01); *G01N 29/043* (2013.01); *G01N 29/225* (2013.01); *G01N 29/2412* (2013.01); *G01N 29/265* (2013.01); *G01M 3/246* (2013.01); *G01N 2291/044* (2013.01);
(Continued)

(58) Field of Classification Search
CPC ............... G01N 29/043; G01N 29/225; G01N 29/2412; G01N 29/265; G01N 2291/044; G01N 2291/106; G01N 2291/2636; G01M 3/005; G01M 3/246; F16L 55/40; F17D 5/06
USPC ......................................................... 73/623
See application file for complete search history.

(56) References Cited

U.S. PATENT DOCUMENTS

| | | |
|---|---|---|
| 3,495,626 A | 2/1970 | Nagel |
| 4,112,850 A | 9/1978 | Sigel-Gfeller |

(Continued)

OTHER PUBLICATIONS

Falck, C., Svendsen, C., and O'Donoghue, A.; "Multi diameter pigging for Asgard;" IBC's Annual 23rd Event Offshore Pipeline Tech; Feb. 28, 2000.
(Continued)

*Primary Examiner* — Lisa M Caputo
*Assistant Examiner* — Rose M Miller
(74) *Attorney, Agent, or Firm* — Mintz Levin Cohn Ferris Glovsky and Popeo, P.C.

(57) ABSTRACT

A sensor carrier module for use in a pipeline pig may include a plurality of skids arranged about an axis of the sensor carrier module, and a flexible section. Each skid typically includes an upstream end, a downstream end, and at least one sensor between the upstream end and the downstream end. Each sensor may be configured to sense a parameter of a wall of a pipeline. The flexible section may be attached to the downstream ends of the skids and to a flange. The flexible section may include wheels configured to roll along the interior surface of the pipeline as the sensor carrier module passes through the pipeline, and a force system to apply a radial force that urges the wheels to interface with the interior surface of the pipeline.

20 Claims, 7 Drawing Sheets

Related U.S. Application Data

(60) Provisional application No. 62/135,340, filed on Mar. 19, 2015.

(51) Int. Cl.
*G01N 29/24* (2006.01)
*F17D 5/06* (2006.01)
*G01M 3/24* (2006.01)

(52) U.S. Cl.
CPC ............ *G01N 2291/106* (2013.01); *G01N 2291/2636* (2013.01)

(56) References Cited

U.S. PATENT DOCUMENTS

| | | | |
|---|---|---|---|
| 4,573,231 A | 3/1986 | Stocksiefen et al. | |
| 5,675,084 A | 10/1997 | Goedecke | |
| 6,023,986 A | 2/2000 | Smith et al. | |
| 6,190,090 B1 | 2/2001 | Campbell et al. | |
| 6,339,993 B1* | 1/2002 | Comello | F16L 55/28 |
| | | | 104/138.2 |
| 8,390,278 B2 | 3/2013 | Petrosky | |
| 10,036,680 B2 | 7/2018 | Frueh | |
| 2003/0136195 A1* | 7/2003 | Krieg | G01N 29/07 |
| | | | 73/628 |
| 2003/0183022 A1 | 10/2003 | Sapelnikov | |
| 2003/0233894 A1 | 12/2003 | Tezuka | |
| 2005/0072237 A1 | 4/2005 | Paige | |
| 2005/0223825 A1* | 10/2005 | Janssen | F16L 55/28 |
| | | | 73/865.8 |
| 2007/0023096 A1 | 2/2007 | Buckley et al. | |
| 2010/0199767 A1* | 8/2010 | Ganin | G01N 29/225 |
| | | | 73/623 |
| 2012/0297882 A1 | 11/2012 | Palma | |
| 2012/0325004 A1 | 12/2012 | Herron et al. | |
| 2013/0025370 A1 | 1/2013 | Herron | |
| 2013/0133429 A1 | 5/2013 | Palma et al. | |
| 2016/0258568 A1 | 9/2016 | Mayorov | |

OTHER PUBLICATIONS

Lindner, H., Beuker, T., and Diekamp, M.; "In-Line Inspection of Multi-Diameter Pipelines: Standardized Development and Testing for a Highly Efficient Tool Fleet;" ROSEN Technology & Research Center, Feb. 28, 2011.

Beuker, T., Brockhaus, S., and Lindner, H.; "Overcoming the specific issues associated with the in-line inspection of gas pipelines;" PPSA Seminar; Dec. 16, 2010.

Bluck, M.; "How to develop and deliver thick wall multi-diameter offshore inspection solutions: A case study;" Annual Technical Seminar of the PPSA; Nov. 14, 2012.

* cited by examiner

FIG. 4

PIPELINE SENSOR CARRIER

CROSS REFERENCE TO RELATED APPLICATIONS

This application is a continuation of U.S. patent application Ser. No. 14/997,125, filed Jan. 15, 2016, entitled "PIPELINE SENSOR CARRIER," which claims priority from and the benefit of U.S. Provisional Patent Application No. 62/135,340, entitled "PIPELINE SENSOR CARRIER," filed Mar. 19, 2015, which is hereby incorporated by reference in its entirety.

BACKGROUND

A pipeline "pig" is typically a tool directed through a section of pipeline, typically advanced through the pipeline by the pressure of fluid flow through the pipeline, or other differences in pressure within the pipeline. Pigs may be used to separate fluid flows within the pipeline, to clean the interior surface of the pipeline, to record geometric information about the pipeline, to inspect the pipeline, as well as for other purposes. One way to inspect the pipeline is to pass a sensor-carrying pig module (e.g., sensor carrier module) through the pipeline. Excessive frictional drag between the sensor-carrying pig module and the interior surface of the pipeline may cause the sensor-carrying pig module (and the sensors) to pull away from the interior wall of the pipeline, thereby reducing the quality of the obtained data. Moreover, the excessive frictional drag between the sensor-carrying pig module and the interior surface of the pipeline may cause excessive wear to the exterior of the sensor-carrying pig module and the pipeline or may prevent the pig from successfully passing through sections of the pipeline in which the inside diameter of the pipeline changes. As such, it would be beneficial to reduce the frictional forces between a sensor carrier module and the interior surface of the pipeline.

BRIEF DESCRIPTION

Several embodiments of the disclosed subject matter are summarized below. These embodiments are not intended to limit the scope of the disclosed subject matter, but rather these embodiments are intended only to provide a brief summary of possible forms of the disclosed subject matter. Indeed, the disclosed subject matter may encompass a variety of forms that may be similar to or different from the embodiments set forth below.

In a first embodiment, a sensor carrier module for use in a pipeline pig may include a plurality of skids arranged about an axis of the sensor carrier module, and a flexible section. Each skid typically includes an upstream end, a downstream end, and at least one sensor between the upstream end and the downstream end. Each sensor may be configured to sense a parameter of a wall of a pipeline. The flexible section may be attached to the downstream ends of the skids and a flange. The flexible section may include wheels configured to roll along the interior surface of the pipeline as the sensor carrier module passes through the pipeline, and a force system to apply a radial force that urges the wheels to interface with the interior surface of the pipeline.

In a second embodiment, a system includes a first sensor assembly and a second sensor assembly. The second sensor assembly is coupled to the first sensor assembly and disposed upstream of the first sensor assembly. Each of the first and second sensor assemblies includes a set of skids and a flexible cone section. The first set of skids may be arranged about an axis. Each skid of the set of skids comprises at least one sensor configured to sense a parameter of a wall of a pipeline. The flexible cone section is coupled to the set of skids and includes one or more wheels that roll along the interior surface of the pipeline as the sensor carrier module passes through the pipeline, and a force system to apply a radial force that urges the wheels to interface with the interior surface of the pipeline. The set of skids of the first sensor assembly may be offset from the skids of the second sensor assembly.

In a third embodiment, a method of inspecting a section of pipeline may include forming a moving seal between a first volume of a first section of pipeline downstream of a pipeline pig and a second volume of a second section of pipeline upstream of the pipeline pig, applying a force to a plurality of wheels, the force may urge the wheels against an interior surface of the pipeline, each wheel may be coupled to a respective slat, maintaining a desired radial distance between ultrasonic transducers and the interior surface of the pipeline, wherein the plurality of ultrasonic transducers on skids may be coupled to the slats, and the wheels may be disposed downstream of the sensors relative to the movement of the pipeline pig through the pipeline, advancing the pipeline pig downstream through the pipeline using a difference between a first pressure in the first volume and a second pressure in the second volume, and logging data from the plurality of ultrasonic transducers as the pipeline pig flows through the section of pipeline.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein:

FIG. 4 is a schematic of an embodiment of the cone section of the exemplary sensor carrier module of FIG. 1;

DETAILED DESCRIPTION

Figure 1:
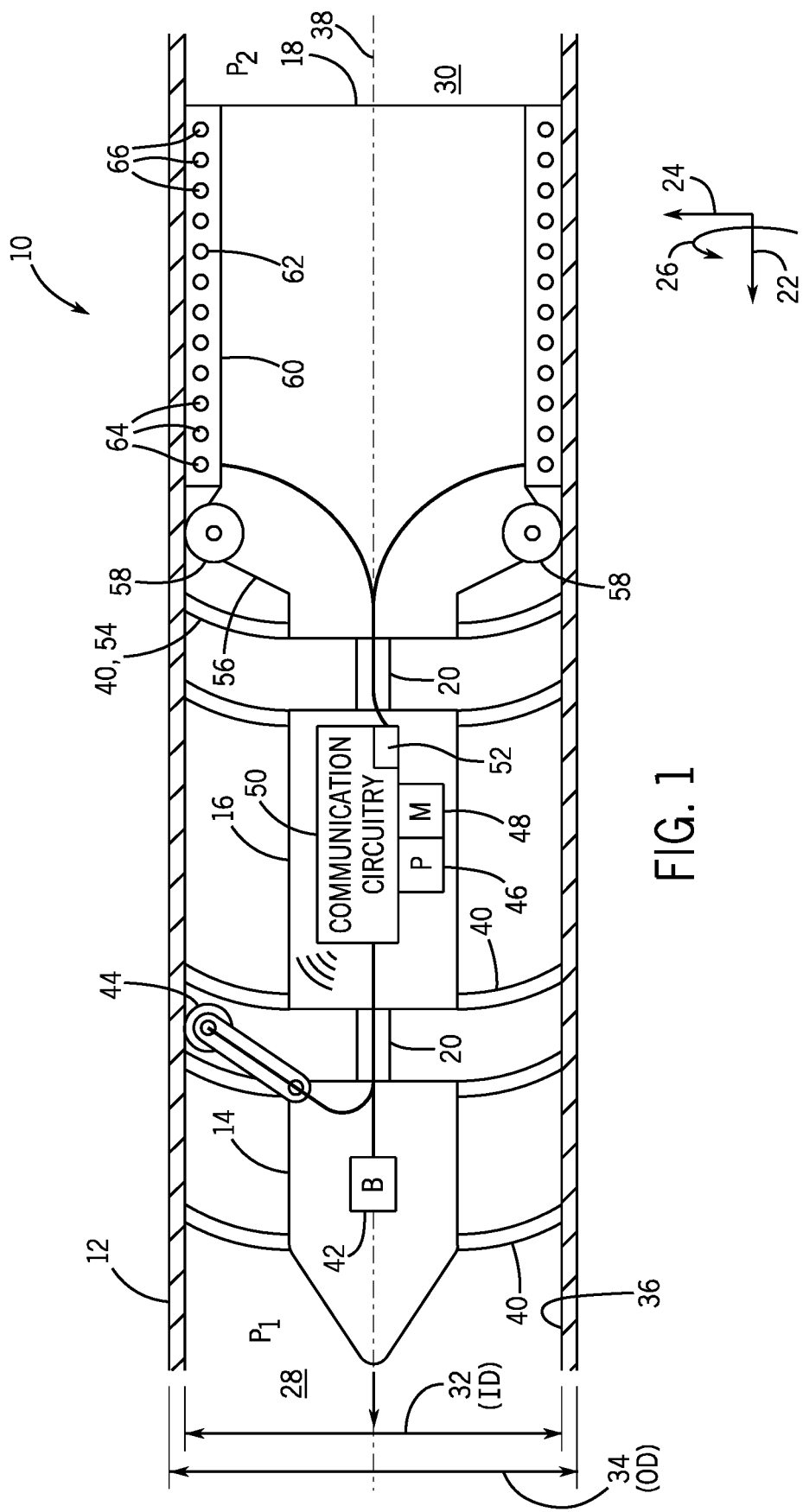
FIG. 1 is a cross-sectional schematic of an embodiment of an exemplary pipeline pig with a sensor carrier module inside a pipeline.

One or more specific embodiments of the disclosed subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The subject matter disclosed herein relates to inspecting fluid pipelines, and more specifically, to reducing the frictional drag between a sensor carrier module of a pipeline pig and the interior surface of a pipe. Over time, cracks, corrosion, or other features may develop in a wall of a section of pipeline. A piece of equipment called a pipeline pig, equipped with sensors may be passed through the section of pipeline in order to detect cracks, corrosion, or other features in the pipeline. Sensor measurements may improve if the sensors are held close to the pipeline wall. However, excessive friction between the pipeline pig and the walls of the pipeline may cause the sensors to separate from the pipeline wall. A pipeline pig having one or more rollers and a force system may enable improved sensor measurements. Specifically, the rollers may reduce friction between the pipeline pig and the pipeline wall. The force system may push the sensors outward, toward the pipeline wall. The rollers and the force system may combine to reduce friction between the pipeline pig and the pipeline wall, while maintaining the sensors close the pipeline wall.

A pipeline may be inspected by passing a pipeline pig with a sensor carrier module through the pipeline. One technique for pipeline inspection uses a series of sensors, such as ultrasonic transducers, piezo ultrasonic transducers, piezocomposite ultrasonic transducers, electromagnetic acoustic transducers (EMATs), magnetic flux sensors, etc. which may be mounted to skids that slide along or otherwise interact with the interior surface of the pipeline. In other embodiments, other kinds of sensors may be used. The sensors may enable a wall-thickness measurement, which may be used to determine the condition of the pipeline, or the presence of cracks, corrosion, or other features.

In certain applications, the sensor measurements may improve if each of the sensors are in close proximity to the interior surface of the pipeline. For example, the sensors may be spaced less than 1 millimeter from the interior surface of the pipe, 100 millimeters from the interior surface of the pipe, or somewhere in between. Unfortunately, excessive friction between the skids and the interior surface of the pipeline may cause the skids (and the sensors) to pull away from the interior wall of the pipeline, thus potentially reducing the quality of the measurement or preventing the obtained measurements from providing a desired resolution and accuracy.

Specifically, the skids may be connected to a flexible cone section, which may be connected to a flange and linkage assembly. The linkage may be connected to other modules, which may be used to pull the sensor carrier through the pipeline. As the sensor carrier is pulled forward by the linkage, frictional drag of the skids on the interior surface of the pipeline may exert a force in the opposite direction. These opposing forces may cause the flexible cone section to lengthen, reducing the angle of the flexible cone section incident to the interior surface of the pipeline, which may result in the skids and the sensors pulling away from the pipeline wall. Furthermore, excessive friction may cause excessive wear to the skids and the pipeline, and excessive friction may prevent the pig from successfully passing through changes in the inside diameter of the pipe.

As such, it may be beneficial to reduce the frictional forces between the sensor carrier module and the interior surface of the pipeline. As discussed in detail below, presently contemplated embodiments may reduce the friction drag on the sensor carrier module via rotational guides such as rollers, balls, and/or wheels positioned between the front sealing/support member of the sensor carrier module and the sensors. The wheels may be biased against the interior surface of the pipeline by one or more springs, or other mechanical, pneumatic, hydraulic, or electric system, or any combination thereof. The wheels may help facilitate passing the pig through a section of pipeline, maintaining the placement of the sensors relative to the interior surface of the pipeline, and extending the life of many of the involved components.

Turning now to the figures, FIG. 1 is a cross-sectional schematic of an exemplary embodiment of a pipeline pig 10 inside a pipeline 12, having a tow (or battery) module 14, a circuitry module 16, and a sensor carrier module 18, connected by linkages 20. For clarity, an axial direction 22, a radial direction 24, and a circumferential direction 26 are shown in FIG. 1. The pipeline 12 may have a downstream end 28, an upstream end 30, an inside diameter 32, an outside diameter 34, and an interior surface 36 (e.g., cylinder interior surface). The pig 10 may have a pig axis 38, which may be substantially aligned with the axis of the pipeline 12.

Each module 14, 16, 18, may have one or more sealing/support members 40 configured to create a seal between the respective module 14, 16, 18 and the interior surface 36 of the pipeline 12, as well as to provide support for, and center, the module 14, 16, 18 in the pipe. Modules 16 and 18 may or may not have one or more sealing members 40. Each of the sealing members 40 may reduce or eliminate fluid flow from one side of the sealing member 40 to the other. In some embodiments, the seals created by sealing members 40 may allow for some fluid flow or some pressure equalization. By sufficiently restricting fluid flow, rather than stopping all fluid flow, the sealing members 40 may achieve their purpose. Each sealing member 40 may be an annular seal structure, which may project or protrude radially outward toward the interior surface 36. The sealing member 40 may include a flat disc-shaped annular seal structure, a first conical seal structure, a curved annular seal structure, or any combination thereof.

In the embodiment shown in FIG. 1, the tow module 14 is the first module in the pig 10. However, the order of modules 14, 16, 18 in the pig 10, and even which modules are included in the pig 10, may vary from embodiment to embodiment. That is, some embodiments of the pig 10 may include a scraping, brushing, cleaning, or attracting (e.g., magnetic) module in addition to a sensor carrier module 18. In some embodiments, the tow module 14 may include a battery 42 used to provide power for any components in the pig 10 such as sensors, processors, memory components, communication circuitry, drive components, pneumatics, hydraulics, etc. In some embodiments, the tow module 14 or the circuitry module 16 may include a measuring wheel 44, configured to measure the distance traveled by the pig 10 in the pipeline 12. In some embodiments, the tow module may include drive components (e.g., motors, pumps, pneumatic components, etc.) to facilitate movement of the pig 10 through the pipeline 12.

The tow module 14 may also include one or more sealing members 40 configured to create a seal between the tow module 14 and the interior surface 36 of the pipeline 12. In some embodiments, the sealing members 40 may be made of a polymer, such as polyurethane. In other embodiments, the sealing members 40 may be made of elastomers, metals, or a combination thereof (e.g., metal coated elastomers). However, it should be understood that the sealing members 40 may be made of any flexible material capable of forming a seal with the interior surface 36 of the pipeline 12. Though FIG. 1 shows one sealing member 40 toward the front of the tow module 14, and one sealing member toward the rear of the tow module 14, the tow module 14 may have a single sealing member, 2, 3, 4, 5, 6, or more sealing members fore and 2, 3, 4, 5, 6, or more sealing members aft, or any other combination of sealing members 40.

In the embodiment shown in FIG. 1, the circuitry module 16 may follow the tow module 14. As previously discussed, in other embodiments, the order of modules may differ among embodiments. The circuitry module 16 may include a processor 46 for executing programs, processing data collected from sensors, and the like. The circuitry module 16 may also include a memory 48 component (e.g., a non-transitory computer readable medium) in communication with the processor 46 that may be used to store data, programs, processing routines, instructions for the processor 46, sensor parameters, etc. The circuitry module 16 may also include communication circuitry 50 configured to communicate data from sensors to the processor 46 and memory 48. The communication circuitry 50 may also communicate collected data to a user or some device wirelessly (e.g., WiFi, Bluetooth, ANT, near field communication, etc.) or through port 52 (e.g., USB, mini or micro USB, CAN, RS232, RS485, or other method of wired data transmission). Data communication may be in real time (i.e., as data is collected), near real time, or after the pig 10 has passed through a section of pipeline 12.

As with the tow module 14, the circuitry module 16 may include one or more sealing members 40 configured to create a seal between the circuitry module 16, and the interior surface 36 of the pipeline 12, and to minimize fluid flow from one side of the sealing member 40 to the other. As with the tow module 14, the circuitry module 16 may have 1, 2, 3, 4, 5, 6 or more sealing members 40.

In the embodiment shown in FIG. 1, the sensor carrier module 18 may follow the circuitry module 16. The sensor carrier module 18, as with the tow module 14 and the circuitry module 16, may have one or more sealing members 40 to create a seal between the sensor carrier module 18, and the interior surface 36 of the pipeline 12, and to minimize fluid flow from one side of the sealing member 40 to the other. The sealing member 40 may also be used to provide support for the sensor carrier module 18 and/or center the sensor carrier module 18 in the pipeline 12. Modules 16 and 18 also may or may not have one or more sealing members 40.

In the embodiment shown in FIG. 1, the leading sealing member 54 of the sensor carrier module 18 may be followed by a flexible section 56 such as a flexible head, hub, curved annular slope, or cone section etc. The flexible section 56 may be a flexible annular structure or assembly, which is configured to expand and contract in the radial direction 24. For simplicity, the section may be described as a flexible cone section in the following discussion. The cone section 56 may include a plurality of parts arranged in a conical shape or be made of a single monolithic piece. The cone section 56 may be made of metal, polyurethane, rubber, plastic, some combination thereof (e.g., metal coated in polyurethane or rubber) or some other flexible material configured to adjust its size to fit inside pipelines 12 of various inside diameters 32. The cone section 56 will be discussed in more detail with regard to FIGS. 2-4.

A plurality of rotational guides 58 such as rollers, balls, or wheels may be attached to the cone section 56, disposed about the cone section 56 in the circumferential direction 26 such that the rotational guides 58 are in contact with the interior surface 36 of the pipeline 12, or separated from the interior surface 36 of the pipeline 12 by a thin film of fluid. Although the rotational guides 58 may be any rotational structure such as rollers, balls, or wheels, the following discussion refers to the rotational guides 58 as wheels for simplicity. However, it should be understood that the wheels 58 are intended to cover any rotational structure that helps to reduce friction. Again, the wheels 58 may be made of metal, polyurethane, plastic, ceramic, or any other suitable material. In some embodiments, the wheels 58 may be of any suitable shape such that they roll along the interior surface 36 of the pipeline 12 as the pig 10 and sensor carrier module 18 move through the pipeline 12. The illustrated embodiments may include any number of wheels 58 (e.g., 1, 2, 3, 4, 5, 6, 7, 8, 9, 10, 11, 12, 13, 14, 15, 20, 30, 40, 50, or more wheels). While this specification focuses on rotational guides, other types of non-rotational guides that reduce friction are also possible.

The plurality of wheels 58 may be coupled to and may be followed by a plurality of slat-shaped skids 60 (e.g., axially extending skids), which may be disposed in the circumferential direction 26 such that the skids 60 are in contact with the interior surface 36 of the pipeline 12, or separated from the interior surface 36 of the pipeline 12 by a thin film of fluid. The skids 60 may include a plurality of sensors 62 disposed in a row or an array down the length of each skid 60.

The sensors 62 may be separated into downstream sensors 64, located near the wheels 58, and upstream sensors 66, located further down the skid 60 from the wheels 58. In some embodiments, the sensors 62 may be recessed from the surface of the skid 60 such that the sensors are spaced within a desired distance from the interior surface 36 of the pipeline. In some embodiments, the sensor 62 may be placed between approximately 0 millimeters and 100 millimeters from the interior surface 36 of the pipeline 12, although larger distances are possible. In other embodiments, the sensor 62 may be placed between approximately 10 millimeters and 50 millimeters from the interior surface 36 of the pipeline 12. In some embodiments, the lower value in the range of acceptable sensor 62 spacing from the interior surface 36 may be 5, 6, 7, 8, 9, 10, 15, 20, 25, 30, 35, 40, 50, 60, 70, 80, 90, or 100 millimeters, or any number in between. Similarly, the higher value in the range of acceptable sensor 62 spacing from the interior surface 36 may be 20, 25, 30, 31, 32, 33, 34, 35, 36, 37, 38, 39, 40, 45, 50, 55, 60, 65, 70, 75, 80, 85, 90, 95, or 100 millimeters, or any number in between.

In general, if the downstream sensors 64 are maintained within the desired spacing with the interior surface 36 of the pipeline 12, the upstream sensors 66 also maintain the desired spacing with the interior surface 36 of the pipeline 12. That is, if the downstream 28 ends of the skids 60 remain in contact, or in near contact with the interior surface 36 of the pipeline, the sensors 62 maintain the desired spacing with the interior surface 36 of the pipeline. The sensors 62 may be ultrasonic transducers, piezo ultrasonic transducers, piezocomposite ultrasonic transducers, electromagnetic acoustic transducers (EMATs), magnetic flux sensors, etc. configured to provide a measurement of the wall thickness of the pipeline 12, or detect or size cracks in the pipeline 12, or any other kind of sensor, which may be used to inspect a section of pipeline 12.

In the present embodiment shown in FIG. 1, the pig 10 may be propelled through a section of pipeline 12 by a difference between the pressure P1 ahead of the pig 10 and the pressure P2 behind the pig 10, as maintained by, for example, the plurality of sealing members 40. The pig 10 may pass through the section of pipeline 12 based upon the pressure of a fluid flowing through the pipeline 12 or based upon fluid pressure using a pump in an upstream direction 30 or downstream direction 28 of the pig. It should be understood, however, that other techniques for pushing, pulling, propelling, or otherwise passing the pig 10 through the section of pipeline 12 may be used. For example, the pig 10 may be pulled through the pipeline 12 using a cable, or the pig 10 may propel itself (e.g., with driven wheels, a conveyer belt like track, etc.) through the section of pipeline 12 using a motor or some other method.

Figure 2:
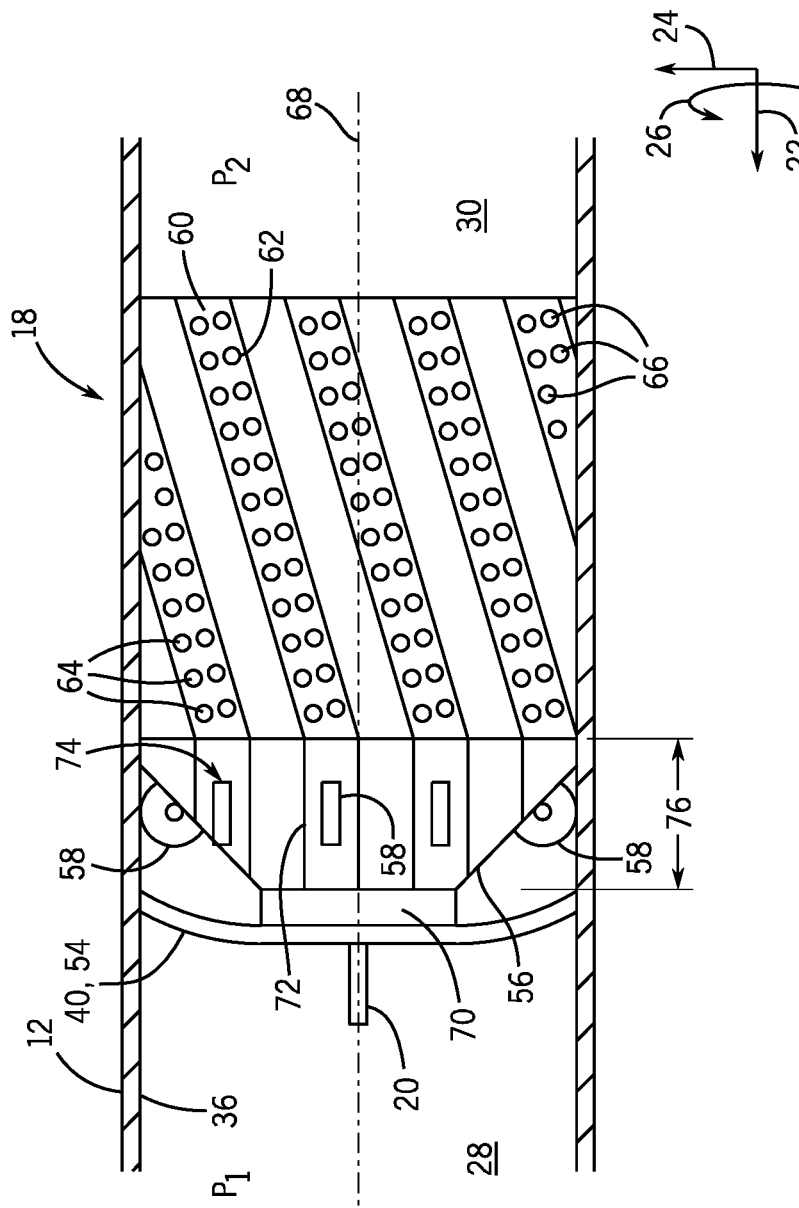
FIG. 2 is a side view of an embodiment of the sensor carrier module of FIG. 1 with the pipeline cutaway.

FIG. 2 shows a side view of an embodiment of the sensor carrier module 18 with the pipeline 12 cutaway. For clarity, FIG. 2 shows a sensor carrier axis 68 through the center of the sensor carrier module 18. As was shown in FIG. 1, a linkage 20 may connect the sensor carrier module 18 to the circuitry module 16 (not shown in FIG. 2). The sensor carrier module 18 may include an additional linkage 20 at the upstream end 30 of the sensor carrier module 18, such that an additional module such as a data collection module, a scraping/cleaning module, a fluid separation module, etc. may trail the sensor carrier module 18 through a section of pipeline 12. For example, in some embodiments, an additional sensor carrier, which may have multiple cone section 56, wheel 58, skid 60 assemblies, may trail the sensor carrier module 18. The linkage 20 may be connected to a flange 70, or some other structural element of the sensor carrier module 18. In the embodiment shown in FIG. 2, a sealing member 40 may be located at the front of the sensor carrier module 18, disposed around the flange 70. Other embodiments may include additional sealing members 40 at various locations along the length of the sensor carrier module 18, or a single sealing member 40 at a different location or no sealing member at all.

The cone section 56 may be coupled to the flange 70. As previously discussed with regard to FIG. 1, the cone section 56 may include a single cone-shaped part, a generally diverging circular arrangement, or a collection of slat-shaped parts arranged in a conical shape. In the embodiment shown in FIG. 2, the cone section 56 may include of a plurality of slats 72 (e.g., cone slats). The slats 72 may be made of metal (e.g., steel, aluminum, stainless steel, titanium, etc.), polyurethane, plastic, rubber, some other suitable material, or a combination thereof. In the present embodiment, the slats 72 may be flexible or resilient to enable the cone section 56 to resiliently expand or contract in the radial direction 24 to adapt to sections of pipeline 12 having varying inside diameters 32, such that the wheels 58 and skids 60 of the sensor carrier module 18 may remain pressed against the interior surface 36 of the pipeline 12.

The cone section 56 may include any number of slats 72, which may be arranged about a carrier axis 68 of the sensor carrier module 18. For example, there may be 6, 7, 8, 9, 10, 12, 14, 16, 18, 20, 22, 24, or more slats 72 or 2 to 100, or any number in between. The carrier axis 68 may be substantially coaxial with the axis 38 of the pig 10 during some sections (e.g., straight) of the pipeline 12. In some embodiments, each slat 72 may have a wheel 58 emerging from a slot or hole 74 in the slat 72, wherein the wheel 58 may be configured to roll along the interior surface 36 of the pipeline 12 as the pig 10 passes through a section of pipeline 12. In other embodiments, there may be fewer wheels 58 than slats 72 or more wheels 58 than slats 72.

As discussed in detail below, some embodiments of the sensor carrier module 18 may include a biasing system to apply an outward biasing force (e.g., in radial direction 24) to push each of the wheels 58 against the interior surface 36 of the section of pipeline 12. For example, this outward biasing force may be applied by the slats 72 (e.g., the slats 72 may operate as leaf springs), a coil spring, a pneumatic piston cylinder assembly, a resilient material, or any combination of biasing forces.

Coupled to the cone section 56 may be a plurality of skids 60. The numbers of skids 60 may or may not correspond to the number of slats 72. For example, in the embodiment shown in FIG. 2, there is a skid 60 coupled to each slat 72. In other embodiments, however, the number of skids 60 may be different from the number of slats 72. There may be any number of skids 60 arranged in a generally annular arrangement. For example, there may be 6, 7, 8, 9, 10, 12, 14, 16, 18, 20, 22, 24, or more skids 60. Each skid 60 may hold a plurality of sensors 62 arranged in a row or an array (e.g., in axial direction 22, circumferential direction 26, or both). In the present embodiment, the sensors 62 include ultrasonic transducers configured to provide an ultrasonic measurement of the pipeline 12 wall thickness, such that cracks, corrosion, or other features may be detected. It should be understood, however, that the sensor carrier module 18 may include any other kind of sensor (e.g., ultrasonic transducers, piezo ultrasonic transducers, piezocomposite ultrasonic transducers, electromagnetic acoustic transducers (EMATs), magnetic flux sensors, etc.) used to sense a parameter of the pipeline wall, or otherwise inspect pipelines 12 using a pig 10.

It should be noted that the skids 60 of the embodiment shown in FIG. 2 may be arranged in a diagonal or a spiral fashion, (e.g., arranged diagonally relative to axial direction 22) such that as the pig 10 moves through the pipeline 12, sensors 62 are disposed around the circumference of the interior surface 36 of the pipeline 12. However, the skids 60 and sensors 62 may be otherwise arranged about the carrier axis 68 in a circumferential direction 26 (e.g., one or more annular rows of sensors 62) to facilitate inspection of substantially the entire circumference of the interior surface 36 of the pipeline 12. In other embodiments, the skids 60 may align with the direction of travel, but may have one or more jogs, shifts, or bends in the same circumferential direction 26, such that sensors 62 are disposed around the entire circumference of the interior surface 36 of the pipeline 12.

In some cases, an improvement in measurements may be achieved when the sensors 62 are in close proximity to the interior surface 36 of the pipeline (e.g., separated from the interior surface 36 of the pipeline 12 by 5 millimeters to 50 millimeters, or anywhere in between.) As such, it may be beneficial to apply an outward (e.g., radial direction 24) biasing force, pushing the skids 60 against the interior surface 36 of the pipeline 12. Techniques for applying this force will be discussed in more detail with regard to FIG. 3. However, the outward biasing force may increase the friction between the sensor carrier module 18 and the interior surface 36 of the pipeline 12.

As the flexible cone section 56 is pulled forward by the linkage 20 and flange 70 and pulled backward by the drag resulting from friction between the skids 60 and the interior surface 36 of the pipeline 12, the length 76 of the cone section 56 may grow, reducing the incident angle of the cone section 56 to the interior surface 36 of the pipeline 12, making it difficult to keep the downstream sensors 64 within the desired difference from the interior surface 36 of the pipeline 12. In order to reduce or eliminate downstream sensor 64 lift-off, an outward (radial) force applied to the upstream end of the cone section 56 may keep the skids 60 pushed against the interior surface 36 of the pipeline 12.

Thus, the wheels 58 may help reduce the friction between the sensor carrier module 18 and the interior surface 36 of the pipeline 12. Additionally, the wheels 58 can allow for a substantial increase in the outward biasing force applied to the wheels 58 without a substantial increase in frictional drag, which may allow the cone section length 76 (and thus, the length of the entire sensor carrier module 18) to be kept short. For example, in some embodiments, the cone section 56 with wheels 58 may have a cone section length 76 of 140 mm, or less than 200 mm, or less than 150 mm, whereas a cone section 56 without wheels 58 may have a cone section length 76 of 380 mm.

Using the design with wheels 58 may result in a decrease in cone section length 76 by more than 60%. Using a cone section 56 with wheels 58 may shorten the length of the sensor carrier module 18 (compared to a sensor carrier module 18 having a cone section without wheels) by more than 25% (from about 1110 mm to less than 900 mm, or about 870 mm). A shorter sensor carrier module 18 may allow the pig to pass through bends in the pipeline 12 with a shorter bend radius than would otherwise be possible. It should be understood, however, that the dimensions of the various components may change as the sensor carrier module 18 is scaled for different sized pipelines 12.

Figure 3:
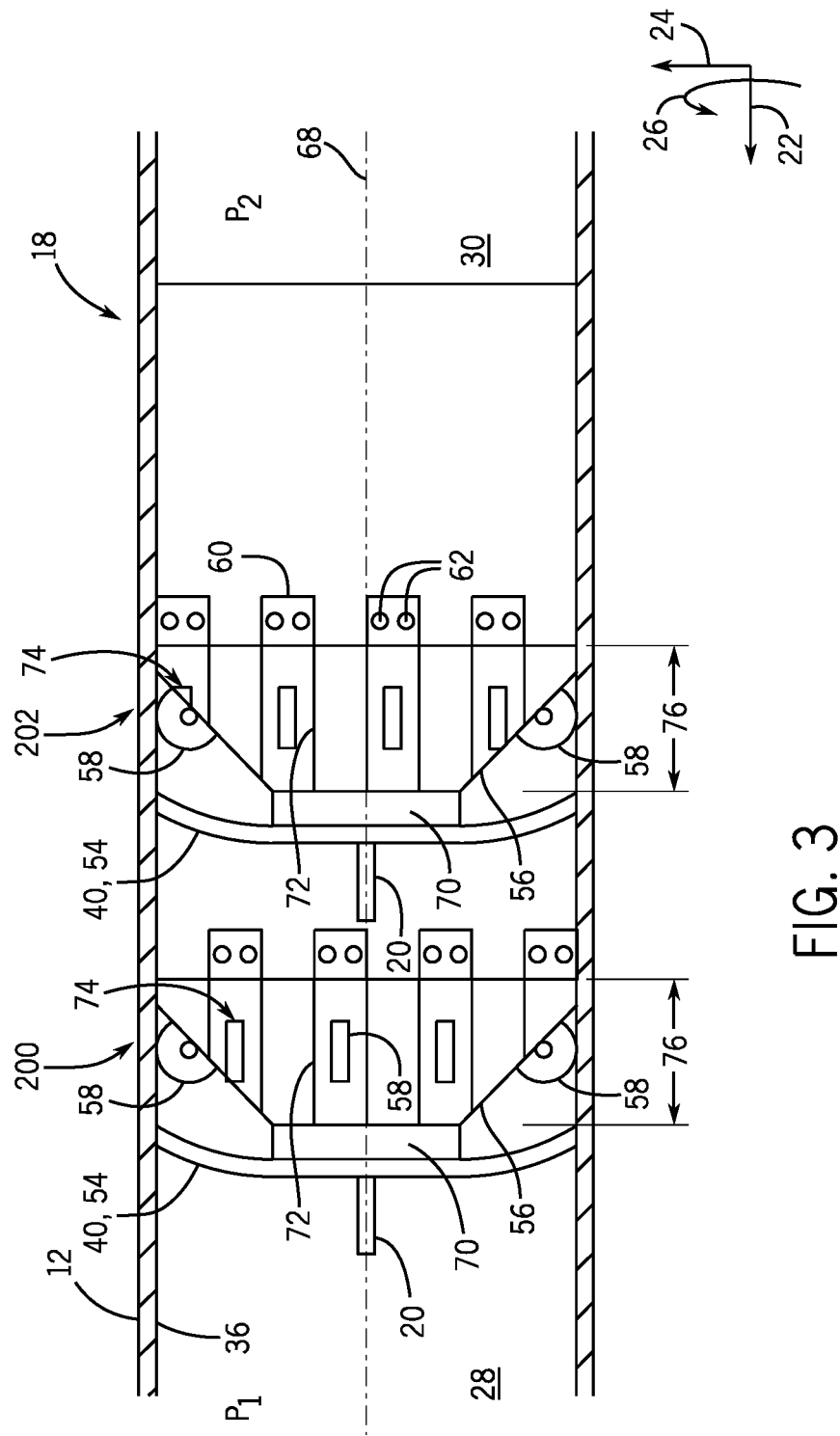
FIG. 3 is a side view of an embodiment of the pipeline pig having two sensor assemblies.

FIG. 3 is a side view of an embodiment of the sensor carrier module 18 having two sensor assemblies 200, 202 (e.g., cone section 56, wheel 58, and skid 60 assemblies). Though the sensor carrier module 18 in FIG. 3 has two sensor assemblies 200, 202, other embodiments of the sensor carrier module 18 may include any number of sensor assemblies 200, 202. For example, the sensor carrier module 18 may have 1, 2, 3, 4, 5, 6, 7, 8, 9, 10, or any other number of sensor assemblies 200, 202. The various sensor assemblies 200, 202 may be connected to one another by one or more linkages 20 disposed at either end 28, 30 of each sensor assembly 200, 202. The linkage 20 may be connected to a flange 70, or some other structural element of the sensor carrier module 18. Each sensor assembly 200, 202 may or may not include a sealing member 40 at the front of the assembly 200, 202, disposed around the flange 70. In some embodiments, one or both of the sensor assemblies 200, 202 may include additional sealing members 40 at various locations along the length of the sensor carrier module 18, or a single sealing member 40 at a different location. In other embodiments, one or both of the sensor assemblies 200, 202 may not contain a sealing member at all. In each sensor assembly 200, 202, the cone section 56 may be coupled to the flange 70. The cone section 56 may include a single cone-shaped part, a generally diverging circular arrangement, or a collection of slat-shaped parts arranged in a conical shape. In the embodiment shown in FIG. 3, the cone section 56 may include a plurality of slats 72 (e.g., cone slats). In the embodiment shown in FIG. 3, the slats 72 may be flexible or resilient to enable the cone section 56 to resiliently expand or contract in the radial direction 24. Accordingly, the cone section 56 may adapt to sections of pipeline 12 having varying inside diameters 32, such that the wheels 58 and skids 60 of the sensor carrier module 18 remain pressed against the interior surface 36 of the pipeline 12.

The cone section 56 may include any number of slats 72, which may be arranged about the carrier axis 68 of the sensor carrier module 18. For example, there may be 6, 7, 8, 9, 10, 12, 14, 16, 18, 20, 22, 24, or any other number of slats 72. In some embodiments, each slat 72 may have a wheel 58 emerging from a slot or hole 74 in the slat 72. The wheel 58 may be configured to roll along the interior surface 36 of the pipeline 12 as the pig 10 passes through a section of pipeline 12. In some embodiments, there may be fewer wheels 58 than slats 72 or more wheels 58 than slats 72. As discussed in detail below, a biasing system may be used to apply an outward biasing force (e.g., in the radial direction 24) to push each of the wheels 58 against the interior surface 36 of the section of pipeline 12. For example, this outward biasing force may be applied by the slats 72 (e.g., the slats 72 may operate as leaf springs), a coil spring, a pneumatic piston cylinder assembly, a resilient material, or any combination of biasing forces.

Coupled to the cone section 56 may be a plurality of skids 60. The numbers of skids 60 may or may not correspond to the number of slats 72. There may be any number of skids 60 arranged in a generally annular arrangement. For example, there may be 6, 7, 8, 9, 10, 12, 14, 16, 18, 20, 22, 24, or more skids 60. In the embodiment shown in FIG. 3, each skid 60 has two adjacent (e.g., radially aligned) sensors 62. However, in other embodiments, each skid 60 may have a plurality of sensors 62 (e.g., upstream sensors 66 and downstream sensors 64) arranged in a row, multiple rows (e.g., as shown in FIG. 2), or an array (e.g., in axial direction 22, circumferential direction 26, or both). In some embodiments, the skids 60 may overlap with one another in the axial direction 22. The sensors 62 may include ultrasonic transducers configured to provide an ultrasonic measurement of the pipeline 12 wall thickness, such that cracks, corrosion, or other features may be detected. It should be understood, however, that the sensor carrier module 18 may include any other kind of sensor (e.g., ultrasonic transducers, piezo ultrasonic transducers, piezocomposite ultrasonic transducers, electromagnetic acoustic transducers (EMATs), magnetic flux sensors, etc.) used to sense a parameter of the pipeline wall, or otherwise inspect pipelines 12 using a pig 10.

The skids 60 of the embodiment shown in FIG. 3 may be arranged such that the skids 60 extend axially parallel to the sensor carrier axis 68, rather than the diagonal or spiral arrangement shown in FIG. 2. The first sensor assembly 200 may be circumferentially offset from the second sensor assembly 202, such that the two sets of skids 60 of the two sensor assemblies 200, 202 are circumferentially offset from one another in an alternating fashion. For example, the sensors 62 on the skids 60 are circumferentially alternated such that the sensors 62 of the first sensor assembly 200 interface along a different circumferential section of the pipeline 12 than the sensors 62 of the second assembly 202 when the sensor carrier module 18 moves along the axis 68. That is, the sensors 62 of the first and second sensor assemblies 200, 202 may together facilitate inspection of substantially the entire circumference of the interior surface 36 of the pipeline 12. The circumferentially offset or circumferentially alternating sets of skids 60 provide sensor 62 coverage all of the way around the circumference of the interior surface 36 pipeline wall of the pipeline 12. Accordingly, as the pig 10 moves through the pipeline 12, sensors 62 are disposed around the circumference of the interior surface 36 of the pipeline 12. As previously discussed, the skids 60 and sensors 62 may be otherwise arranged about the carrier axis 68 in a circumferential direction 26 (e.g., one or more annular rows of sensors 62) to facilitate inspection of substantially the entire circumference of the interior surface 36 of the pipeline 12. In other embodiments, the skids 60 may align with the direction of travel, but may have one or more jogs, shifts, or bends in the same circumferential direction 26, such that sensors 62 of the sensor carrier module 18 are disposed around the entire circumference of the interior surface 36 of the pipeline 12.

Figure 4:
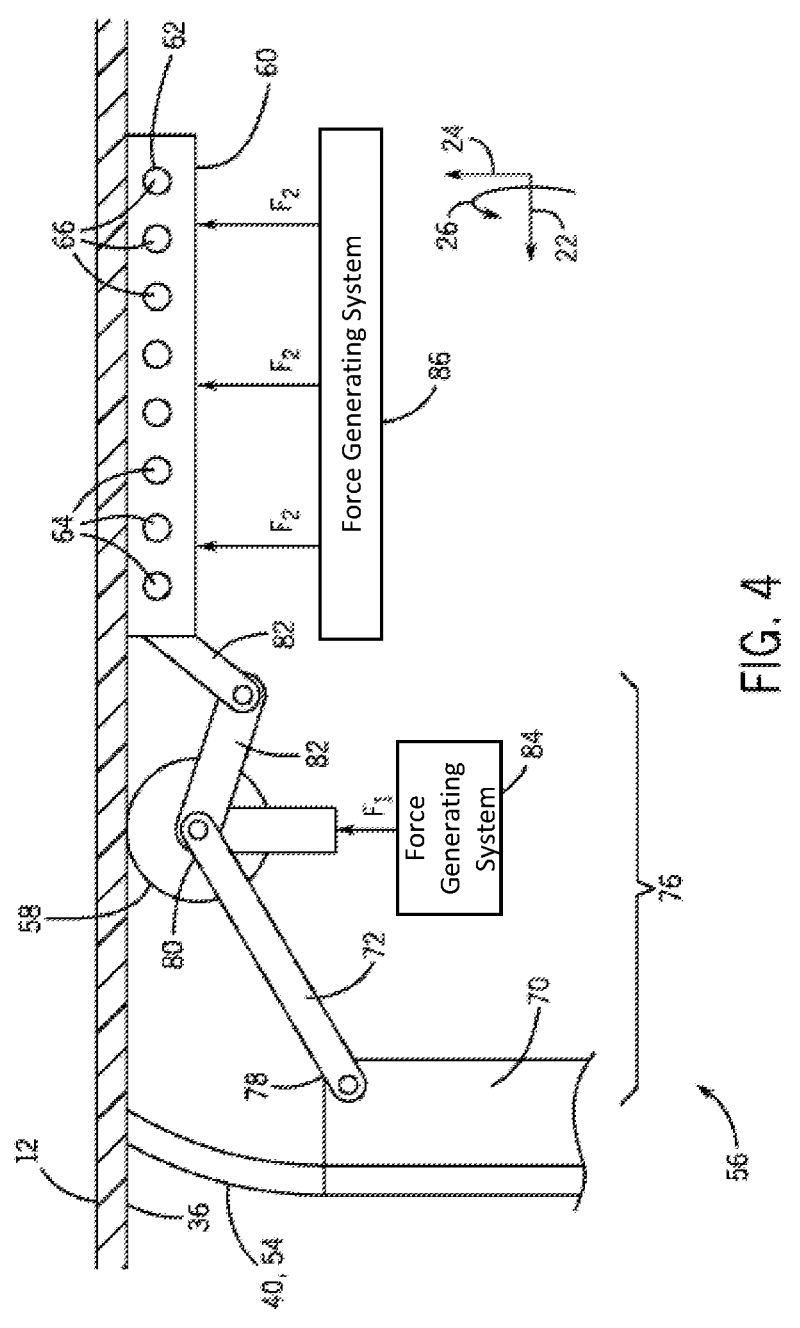

FIG. 4 is a schematic of an exemplary embodiment of the cone section 56 of the sensor carrier module 18 shown in FIGS. 1 and 2. One of the slats 72 is illustrated as a linkage pinned to the flange 70 on the downstream end 78, and pinned to the wheel 58 on the upstream end 80. It should be understood, however, that FIG. 4 shows one embodiment and other configurations are possible. In some embodiments, the skid 60 may be directly linked to the wheel 58. In other embodiments, one or more linkages 82 may couple the skid 60 to the wheel 58. The linkages may be pinned, rigid, or some combination thereof. In some embodiments, a single L-shaped or curved linkage 82 may be used. A force $F_1$ (e.g., biasing force) may be applied to the wheel 58 by the force generating system 84 (e.g. a v-shaped leaf spring, or another kind of spring), which can urge the wheel 58 against the interior surface 36 of the pipeline 12. The force generating system 84 can urge, via the wheel 58 and linkages 82, the skid 60 against the interior surface 36 of the pipeline 12. Additionally, or in the alternative, a force $F_2$ (e.g., biasing force) may be applied to the skid 60 by the first force generating system 84 or a second force system 86 to push the skid 60 against the interior surface 36 of the pipeline 12.

The forces $F_1$, $F_2$ may be applied by a spring (e.g., a leaf spring, a leg spring, a coil spring, a gas spring, or some other kind of spring), a mechanical actuator, a pneumatic actuator (e.g., a piston cylinder assembly), a hydraulic actuator (e.g., a piston cylinder assembly), or an electric actuator (a D.C. motor, a servo, etc.). In another embodiment, the forces $F_1$, $F_2$ may be applied by the spring-like flexibility of an elastic, resilient material (e.g., elastomer, polymer, polyurethane, rubber, etc.) of the slat 72, which may not typically be considered a spring.

Forces $F_1$ and $F_2$ may or may not be equal in magnitude. In some embodiments, $F_1$ may be greater than $F_2$. In other embodiments, $F_2$ may be greater than $F_1$. Furthermore, the force generating system 84 may include a damping component. In some embodiments, the slats 72 may be attached to the flange 70 as a cantilever and then act as a leaf spring, such that the slats 72 may act as the force generating system 84. As previously discussed, the wheel 58 may reduce the friction between the sensor carrier module 18 and the interior surface 36 of the pipeline 12. Additionally, or in the alternative, the wheels 58 may enable the outward biasing force $F_1$ to increase without substantially increasing the friction while maintaining the skids 60 in contact with, and the sensors 62 within a desired threshold distance of, the interior surface 36 of the pipeline 12.

One possible advantage of the techniques described herein is the ability to more easily pass through transitions in the inside diameter 32 of a section of pipeline 12. Once the tow module 14 passes from a smaller diameter section to a larger diameter section, the ability of the sealing members 40 of the tow module 14 to form a seal with the interior surface 36 of the pipeline, and thus the ability of the tow module 14 to pull the sensor carrier module 18, may be reduced without the disclosed embodiments. Furthermore, without the disclosed embodiments, because the sensor carrier module 18 is still in the section of pipeline 12 with a smaller inside diameter 32, the frictional drag between the sensor carrier module 18 and the interior surface 36 of the pipeline 12 may be substantial enough that the tow module 14 may have difficulty pulling the sensor carrier module 18 through the transition. However, in accordance with the disclosed embodiments, when the sensor carrier module 18 is equipped with wheels 58, the frictional drag between the sensor carrier module 18 and the interior surface 36 of the pipeline 12 may be reduced such that the tow module 14 is capable pulling the sensor carrier module 18 through the transition.

Figure 5:
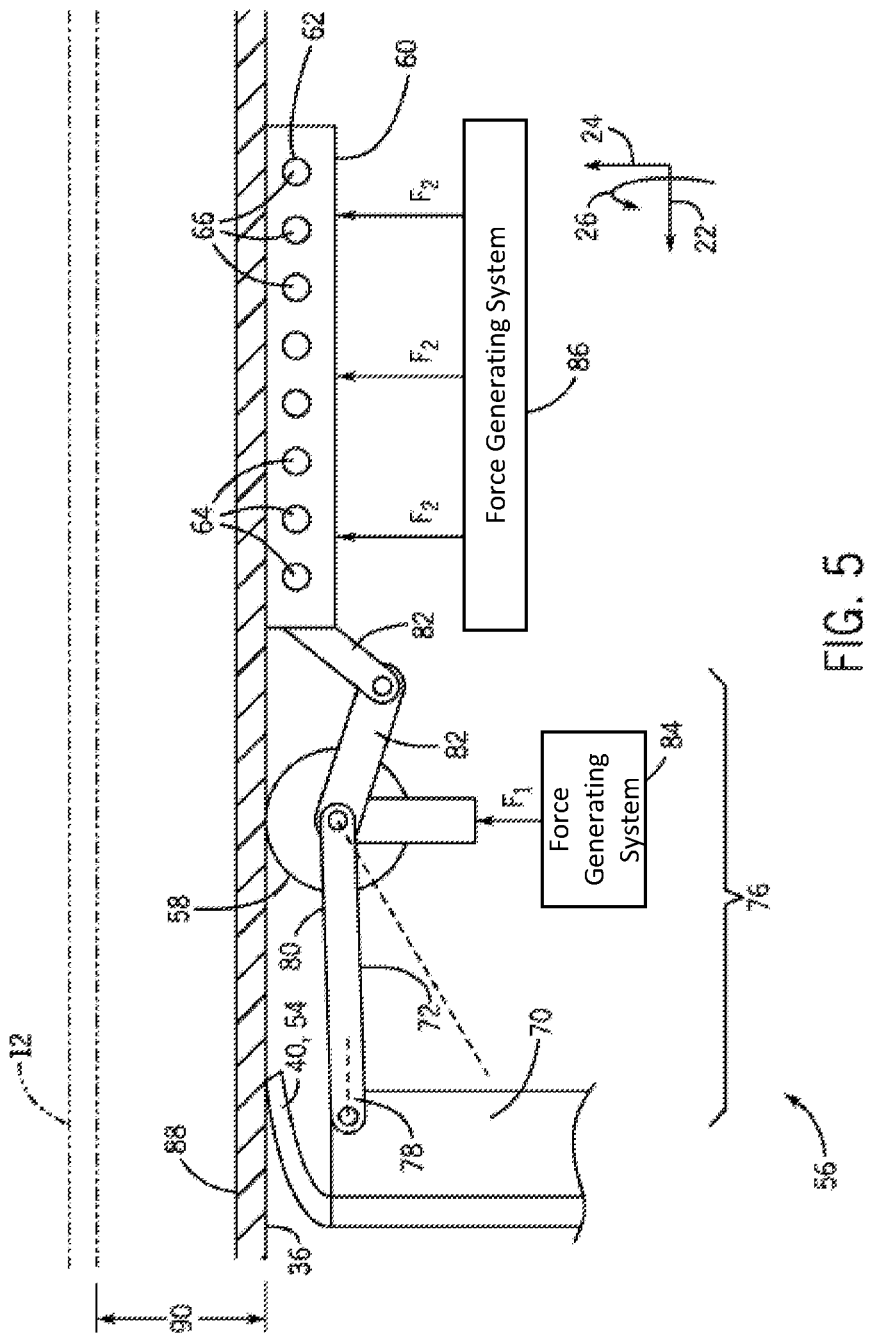
FIG. 5 is a schematic of an embodiment of the cone section of the exemplary sensor carrier module in a section of pipeline with a smaller inside diameter than that shown in FIG. 1.

FIG. 5 is a schematic of an exemplary embodiment of the cone section 56 of the sensor carrier module 18 in a section of pipeline 88 with a smaller inside diameter than that shown in FIGS. 1-4. The decrease 90 is the decrease in the inside radius of the pipeline, or one half the decrease in inside diameter 32. For clarity, the larger pipeline 12, shown in FIGS. 1-4, having inside diameter 32 is shown with dotted lines. As the sensor carrier module 18 enters the smaller diameter section of pipeline 88, the sealing members 40, 54 may bend backward to conform to the interior surface 36 of the pipeline 88. Additionally, the slats 72 may pivot or bend about the flange 70, contacting the cone section 56 in the radial direction 24, in order to keep the wheels 58, and the skids 60 in contact (or near contact) with the interior surface 36 of the pipeline 88, such that the desired spacing between the sensors 62, 64, 66 and the interior surface 36 of the pipeline 88 is maintained.

Similarly, when the sensor carrier module 18 enters a section of pipeline 12 with a larger inside diameter, the sealing members 40, 58, and slats 72 may pivot or bend about the flange 70 in the opposite direction, expanding the cone section 56 in the radial direction 24, in order to keep the wheels 58, and the skids 60 in contact (or near contact) with the interior surface 36 of the pipeline 12, such that the desired spacing between the sensors 62, 64, 66 and the interior surface 36 of the pipeline 12 may be maintained.

Another possible advantage of the techniques described herein is that the addition of wheels 58 may allow for a reduction in the length of the cone section 56 (thus reducing the total length of the sensor carrier module 18), so the pig may navigate bends in the pipeline 12 more easily. Specifically, by reducing the frictional drag between the interior surface 36 of the pipeline 12 and the sensor carrier module 18, the addition of wheels 58 may allow for increased force $F_1$ (e.g., outward biasing force), which may allow for steeper cone section 56 angles. Steeper cone section 56 angles, configured for the same maximum pipeline 12 diameter may allow for the shortening of the cone section 56. As the total length of the sensor carrier module 18 decreases, the sensor carrier module 18, and by extension the pig 10, may be capable of navigating tighter radius bends in the pipeline 12.

Another possible advantage of the techniques described herein is that the addition of wheels 58 may expand the range of diameters to which the cone section 56 can expand/collapse, effectively expanding the range of pipeline 12 sizes the pig 10 may navigate. As previously discussed, the addition of wheels 58 may allow for increased force $F_1$ (e.g., outward biasing force), which may allow for steeper cone section 56 angles. If the lengths of the slats 72 are kept long, the cone section 56 may expand to larger diameters. As a result, the sensor carrier module 18, and by extension the pig 10, may be capable of navigating pipelines 12 with a wider range of inside diameters 32.

Additionally, by reducing the friction between the sensor carrier module 18 and the interior surface 36 of the pipeline 12, the addition of wheels 58 may reduce the wear of parts in contact with the interior surface 36 of the pipeline 12 (e.g., the slats 72 or other cone elements, the sealing members 40, the skids 60, and the like). Reduction of frictional drag may also decrease wear of the pipeline 12. Decreased wear may increase the usable lifespans of both the parts of the sensor carrier module 18 and the pipeline 12.

Figure 6:
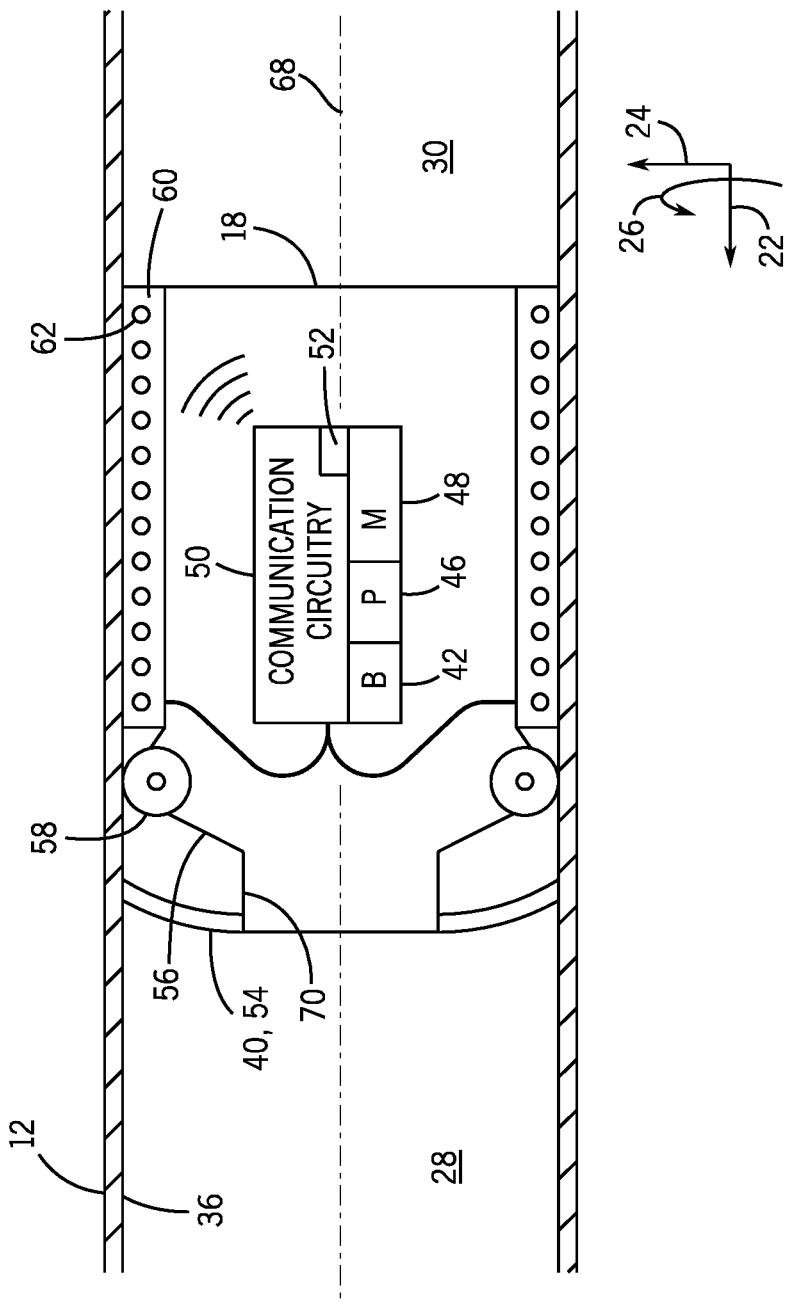
FIG. 6 is a schematic of an exemplary embodiment of a pipeline pig with a sensor carrier module inside a pipeline, different from that shown in FIG. 1.

FIG. 6 is a schematic of an exemplary embodiment of the pipeline pig 10 with a sensor carrier module 18 inside a pipeline 12. As can be seen in FIG. 6, the sensor carrier module 18 may include a battery 42, processor 46, memory 48, communication circuitry 50, and communication port 52. In the embodiment shown in FIG. 6, a pig may have a single module (i.e., sensor carrier module 18), or any number of additional modules previously discussed. Furthermore, it should be understood that FIG. 6 is intended to show that the location of certain components of the pig 10 may be flexible. That is, in some embodiments, the various components (e.g., battery 42, processor 46, memory 48, communication circuitry 50, and communication port 52) may be disposed across multiple modules. In other embodiments, the components may be consolidated into a single module.

Figure 7:
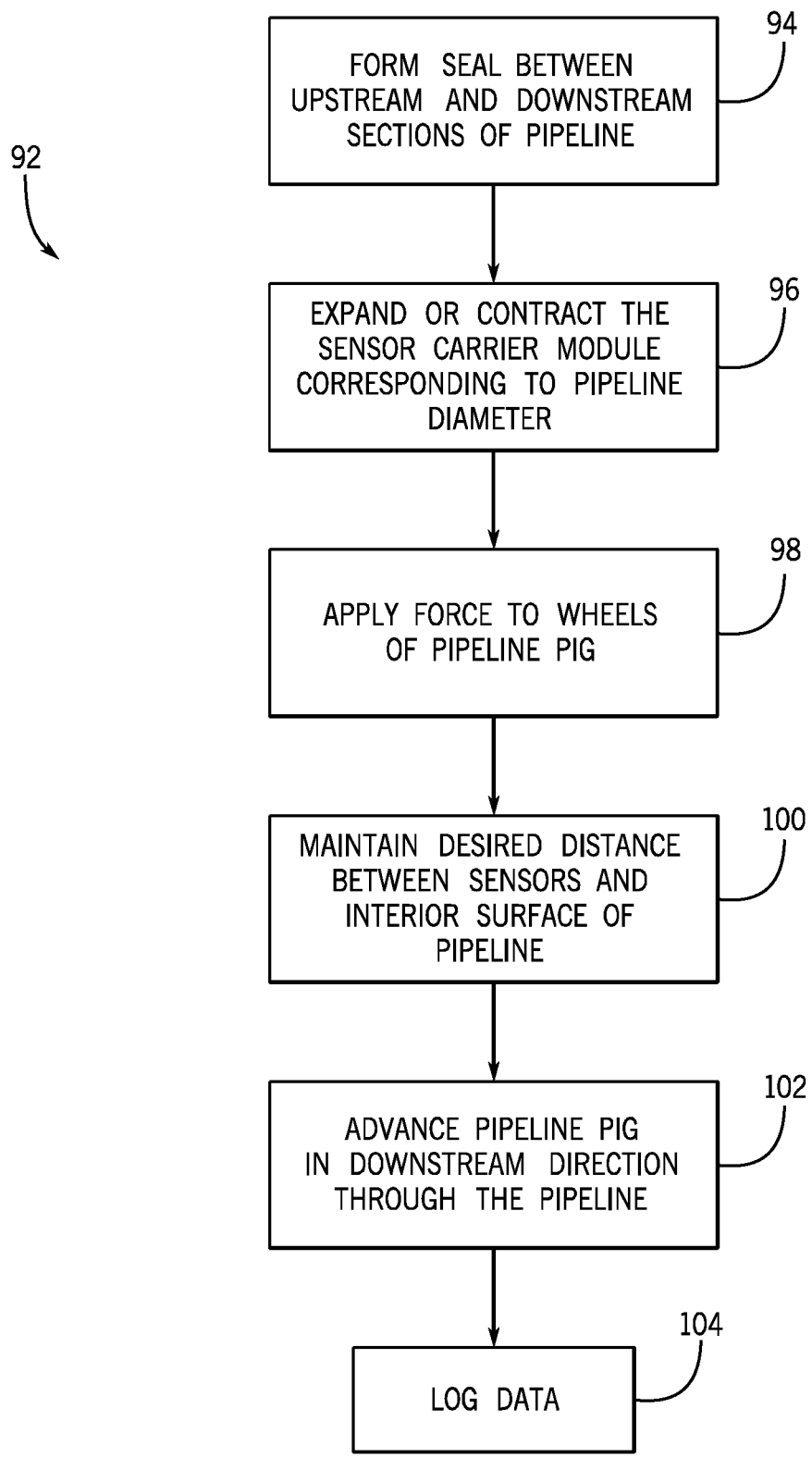
FIG. 7 is a flow chart showing an exemplary embodiment of a process for inspecting a pipeline.

FIG. 7 is a flow chart showing an exemplary embodiment of a process 92 for inspecting a pipeline. The process 92 is exemplary only and not limiting. The process 92 may be altered by, for example, having blocks added, removed, and/or rearranged. In block 94, the process 92 may form a seal between a first volume of the section of the pipeline downstream 28 of the pipeline pig 10 and a second volume of the section of the pipeline upstream 30 of the pipeline pig 10. The seal may be formed using one or more sealing members 40 disposed along the length of the pipeline pig 10. It should be understood however, that sealing members 40 may allow for some fluid flow or pressure equalization. As previously discussed, the sealing members 40 may be made of a polymer, such as polyurethane, or elastomers, metals, or a combination thereof (e.g., metal coated elastomers). It should be understood, however, that the sealing members 40 may be made of any flexible material capable of forming a seal with the interior surface 36 of the pipeline 12.

In block 96, the process 92 may expand or contract the sensor carrier module 18 corresponding to the inside diameter 32 of the pipeline 12. As previously discussed, the flexible cone section 56 may be configured to radially expand and contract to fit inside of sections of pipeline 12 having a range of inside diameters 32. For example, in some embodiments, the flexible cone section 56 may include an annular array of slats 72 coupled to wheels 58, which may be coupled to skids 60 supporting sensors 62. The wheels 58 may be subject to an outward biasing force $F_1$ that pushes the wheels, and in some embodiments the skids 60, against the interior surface 36 of the pipeline. The flexible cone section 56 may expand or contract such that the wheels 58 and skids 60 may remain in contact, or near contact, with the interior surface 36 of sections of pipeline 12 having a range of inside diameters 32.

In block 98, the process 92 may apply a radially outward biasing force $F_1$ to the wheels 58 to urge the wheels against the interior surface 36 of the pipeline 12. The outward biasing force $F_1$ may be applied by a force system 84, which may include a spring (e.g., a leaf spring, a leg spring, a coil spring, a gas spring, or some other kind of spring), a mechanical actuator, a pneumatic actuator (e.g., a piston cylinder assembly), a hydraulic actuator (e.g., a piston cylinder assembly), or an electric actuator (a D.C. motor, a servo, etc.). Each wheel 58 may or may not be coupled to a respective slat 72.

In block 100, the process 92 may maintain the desired radial distance between the sensors, such as ultrasonic transducers, and the interior surface 36 of the pipeline 12. The desired distance may be between approximately 0 millimeters and 100 millimeters from the interior surface 36 of the pipeline 12, although larger distances are possible. In other embodiments, the sensor 62 may be placed between approximately 10 millimeters and 50 millimeters from the interior surface 36 of the pipeline 12. In some embodiments, the lower value in the range of acceptable sensor 62 spacing from the interior surface 36 may be 5, 6, 7, 8, 9, 10, 15, 20, 25, 30, 35, 40, 50, 60, 70, 80, 90, or 100 millimeters, or any number in between. Similarly, the higher value in the range of acceptable sensor 62 spacing from the interior surface 36 may be 20, 25, 30, 31, 32, 33, 34, 35, 36, 37, 38, 39, 40, 45, 50, 55, 60, 65, 70, 75, 80, 85, 90, 95, or 100 millimeters, or any number in between.

In block 102, the process 92 may advance the pipeline pig 10 through a section of pipeline 12 by a difference between the pressure P1 downstream 28 of the pig 10 and the pressure P2 upstream 30 of the pig 10. The pig 10 may pass through the section of pipeline 12 based upon the pressure of a fluid flowing through the pipeline 12 or based upon fluid pressure using a pump in an upstream direction 30 or downstream direction 28 of the pig. Other techniques for pushing, pulling, propelling, or otherwise passing the pig 10 through the section of pipeline 12 may be used. For example, the pig 10 may be pulled through the pipeline 12 using a cable, or the pig 10 may propel itself (e.g., with driven wheels, a conveyer belt like track, etc.) through the section of pipeline 12 using a motor or some other method.

In block 104, the process 92 may log data from the sensor 62. The data may be ultrasonic measurements indicative of the thickness of portions of the pipeline 12, the presence of cracks in the pipeline 12, the size of cracks in the pipeline 12, or other data. The data may be stored in the memory component 48 of the pipeline pig, immediately communicated by the communication circuitry 50, or stored or communicated in some other way.

In a first embodiment, a sensor carrier module for use in a pipeline pig, may include a plurality of skids arranged about an axis of the sensor carrier module, and a flexible section. Each skid typically includes an upstream end, a downstream end, and sensors between the upstream end and the downstream end. Each sensor may be configured to sense a parameter of a wall of a pipeline. The flexible section may be attached to the downstream ends of the skids and a flange. The flexible section may include wheels configured to roll along the interior surface of the pipeline as the sensor carrier module passes through the pipeline, and a force system to apply a radial force that urges the wheels to interface with the interior surface of the pipeline. In some embodiments, the sensors may be ultrasonic transducers, or other types of sensors used to inspect a section of pipeline. The cone section may be a single part, a collection of slat-shaped components, or some other combination of parts. The force system may be a spring (e.g., a v-shaped leaf spring), or the force may be applied by some other method (pneumatics, hydraulics, etc.). In some embodiments, a force may also be applied to the skids, pressing the sensors radially toward the interior surface of the section of pipeline. The pipeline pig may be passed through a section of pipe using pressure differences in the pipe (naturally occurring, created by a pump, or some other way), or the pipeline pig may be pulled through the section of pipeline or driven with a motor, or moved by a mechanism that generates a stepping motion.

This written description uses examples to describe the disclosed subject matter, including the best mode, and also to enable any person skilled in the art to practice the invention, including making and using any devices or systems and performing any incorporated methods. The patentable scope of the disclosed subject matter is defined by the claims, and may include other examples that occur to those skilled in the art.

The invention claimed is:

1. A pipeline pig, comprising:
   at least one sensor carrier module comprising
      a flange,
      a flexible annular cone section disposed about a longitudinal axis of the at least one sensor carrier module, the flexible annular cone section including
         a slat having a first end and second end, the first end coupled to the flange, and
         at least one guide coupled to the second end of the slat and configured to travel within an interior surface of a pipeline as the at least one sensor carrier module passes through the pipeline,
      a linkage coupled to the at least one guide,
      a plurality of skids coupled to the flexible annular cone section, wherein each skid of the plurality of skids includes
         an upstream end,
         a downstream end, wherein each skid is only coupled to the linkage at the downstream end of the skid, and
         a plurality of sensors disposed between the upstream end and the downstream end, wherein the plurality of sensors are configured to sense a parameter of a wall of the pipeline, and
      a first force system configured to apply a first radial force that urges the at least one guide and each skid of the plurality of skids to interface with the interior surface of the pipeline.

2. The pipeline pig of claim 1, wherein the at least one guide is configured to reduce friction with the interior surface of the pipeline.

3. The pipeline pig of claim 1, wherein the plurality of sensors comprise a plurality of ultrasonic transducers.

4. The pipeline pig of claim 1, wherein further comprising a sealing member coupled to the flange.

5. The pipeline pig of claim 1, wherein each of the slat comprises a polymer-coated metal.

6. The pipeline pig of claim 1, wherein the first force system comprises a spring.

7. The pipeline pig of claim 1, further comprising a second force system configured to apply a second radial force configured to press each skid of the plurality of skids against the interior surface of the pipeline.

8. The pipeline pig of claim 1, further comprising:
   a tow module coupled to the sensor carrier module, the tow module comprising:
      one or more tow module sealing members; and
      a battery; and
   a circuitry module coupled to the tow module, the circuitry module comprising:
      one or more circuitry module sealing members;
      a processor; and
      a memory component.

9. The pipeline pig of claim 8, wherein the plurality of sensors is communicatively coupled to the circuitry module for data logging.

10. The pipeline pig of claim 8, further comprising a measuring wheel configured to measure a distance traveled by the pipeline pig through the pipeline.

11. The pipeline pig of claim 1, wherein the at least one guide includes a rotational guide.

12. The pipeline pig of claim 1, wherein the first force system includes an electric actuator.

13. The pipeline pig of claim 1, wherein each slat of the plurality of slats is coupled to the flange in a cantilevered configuration at a first end of the cone section and coupled to the at least one guide at a second end of the cone section, the cantilevered configuration providing a radial force to the at least one guide.

14. A pipeline pig, comprising:
   at least one sensor carrier module comprising
      a flange having a leading end and a trailing end,
      a flexible annular cone section disposed about a longitudinal axis of the at least one sensor carrier module and coupled at an upstream end to the trailing end of the flange, the flexible annular cone section including
         a slat having a first end and second end, the first end coupled to the trailing end of the flange, and
         at least one guide coupled to the second end of the slat and configured to contact and reduce friction with an interior surface of a pipeline wall,
      a linkage coupled to the at least one guide,
      a plurality of skids coupled at an upstream end to a trailing end of the flexible annular cone section, wherein each skid of the plurality of skids includes an upstream end and a downstream end and each skid of the plurality of skids is only coupled to the linkage at the downstream end of each skid, each skid of the plurality of skids having a plurality of sensors mounted thereon and configured to sense a parameter of a wall of a pipeline, and the flexible cone annular section coupled between the flange and each skid of the plurality of the skids, and
      a force system coupled to the flexible annular cone section and configured to apply a radial force that urges the at least one guide and each skid of the plurality of skids to interface with the interior surface of the pipeline.

15. The system of claim 14, wherein the plurality of skids are coupled at only the leading end to the flexible annular cone section.

16. The system of claim 14, wherein the plurality of skids are spaced circumferentially around the longitudinal axis of the sensor carrier module.

17. The system of claim 14, wherein at least one sensor of the plurality of sensors comprises an ultrasonic transducer.

18. The system of claim 14, wherein the force system comprises a spring.

19. A method of inspecting a pipeline, comprising:
   advancing a pipeline pig into an interior volume of a pipeline such that a moving seal is formed between a first volume of a first section of pipeline downstream of the pipeline pig and a second volume of a second section of pipeline upstream of the pipeline pig, the pipeline pig having at least one sensor carrier module including a flange, a flexible annular cone section disposed about a longitudinal axis of the at least one sensor carrier module, the flexible annular cone section including a slat having a first end and a second end, the first end coupled to the flange, and at least one guide coupled to the second end of the slat and configured to travel within an interior surface of the pipeline as the at least one sensor carrier module passes through the pipeline, wherein the sensor carrier module includes a linkage coupled to the at least one guide and a plurality of skids coupled to the flexible annular cone section, each skid of the plurality of skids including an upstream end, a downstream end, wherein each skid is only coupled to the linkage at the downstream end of the skid, and wherein the plurality of skids includes a plurality of ultrasonic transducers disposed between the upstream end and the downstream end, the plurality of ultrasonic transducers configured to sense a parameter of a wall of the pipeline, wherein the at least one sensor carrier module includes a force system configured to apply a radial force that urges the at least one guide and each skid of the plurality of skids to interface with the interior surface of the pipeline;

advancing the pipeline pig in the downstream direction through the pipeline using a difference between a first pressure in the first volume and a second pressure in the second volume; and logging data from the plurality of ultrasonic transducers as the pipeline pig flows through the section of pipeline.

20. The method of claim 19, wherein the data comprises ultrasonic measurements indicative of a thickness of portions of the pipeline, one or more cracks in the pipeline, and a size of the one or more cracks in the pipeline.

* * * * *